United States Patent
Kim et al.

(10) Patent No.: US 7,095,503 B2
(45) Date of Patent: Aug. 22, 2006

(54) METHOD OF FULL-COLOR OPTICAL COHERENCE TOMOGRAPHY

(75) Inventors: Myung K. Kim, Tampa, FL (US); Lingfeng Yu, Tampa, FL (US)

(73) Assignee: University of South Florida, Tampa, FL (US)

( * ) Notice: Subject to any disclaimer, the term of this patent is extended or adjusted under 35 U.S.C. 154(b) by 185 days.

(21) Appl. No.: 11/063,499

(22) Filed: Feb. 22, 2005

(65) Prior Publication Data

US 2005/0185192 A1 Aug. 25, 2005

Related U.S. Application Data

(60) Provisional application No. 60/635,162, filed on Dec. 10, 2004, provisional application No. 60/546,408, filed on Feb. 20, 2004.

(51) Int. Cl.
*G01B 9/02* (2006.01)

(52) U.S. Cl. .................................................. 356/497

(58) Field of Classification Search ............. 356/479, 356/496, 497
See application file for complete search history.

(56) References Cited

U.S. PATENT DOCUMENTS

| | | | |
|---|---|---|---|
| 4,641,971 A * | 2/1987 | Korth | 356/497 |
| 6,057,920 A * | 5/2000 | Fercher et al. | 356/497 |
| 6,498,948 B1* | 12/2002 | Ozawa et al. | 600/476 |

OTHER PUBLICATIONS

Bordenave et al., Wide-Field Optical Coherence Tomography: Imaging of Biological Tissues, Applied Optics, Apr. 2002, p. 2059-2064, vol. 41 No. 10.

Dakoff et al., Microscopic Three-Dimensional Imaging by Digital Interference Holography, Journal of Electronic Imaging, Oct. 2003, p. 1-5, vol. 12(4).

Ding et al., Real-Time Phase-Resolved Optical Coherence Tomography and Optical Doppler Tomography, Optics Express, Mar. 2002, p. 236-245, vol. 10 No. 5.

Dubois et al., High-Resolution Full-Field Optical Coherence Tomography with a Linnik Microscope, Applied Optics, Feb. 2002, p. 805-812, vol. 41 No. 4.

Ducros et al., Parallel Optical Coherence Tomography in Scattering Samples Using a Two-Dimensional Smart-Pixel Detector Array, Optics Communications, 2002, 29-35, vol. 202.

Fercher et al., Optical Coherence Tomography—Principles and Applications, Reports on Progress in Physics, 2003, p. 239-303, vol. 66 (2003).

Hitzenberger et al., Three-dimensional Imaging of the Human Retina by High-Speed Optical Coherence Tomography, Optics Express, 2003, p. 2753-2761, vol. 11 No. 21.

(Continued)

*Primary Examiner*—Gregory J. Toatley, Jr.
*Assistant Examiner*—Michael A. Lyons
(74) *Attorney, Agent, or Firm*—Smith & Hopen, P.A.; Molly L. Sauter (57) ABSTRACT

Two-dimensional and three-dimensional optical coherence tomography is obtained by differential imaging of full-frame interference images using a white light source. Full-color tomographic imaging is also possible by processing the three-color channels of the interference images. A technique is described to obtain two-dimensional OCT images with full natural color representation. In a particular embodiment, the interference image is acquired using a color camera and the three-color channels are processed separately, recomposing the final image. In an additional embodiment, the interference images are acquired using separate red, blue and green light sources and the three color channels are combined to recompose the final image.

20 Claims, 12 Drawing Sheets
(8 of 12 Drawing Sheet(s) Filed in Color)

OTHER PUBLICATIONS

M.K. Kim, Tomographic Three-dimensional Imaging of a Biological Specimen Using Wavelength-Scanning Digital Interference Holography, Optics Express, 2000, 305-310, vol. 7 No. 9.

Laude et al., Full-Field Optical Coherence Tomography with Thermal Light Applied Optics, Nov. 2002, p. 6637-6645, vol. 41 No. 31.

Neil et al., Method of Obtaining Optical Sectioning by Using Structured Light in a Conventional Microscope, Optics Letters, 1997, p. 1905-1907, vol. 22 No. 24.

Sando et al., Color-Computer-Generated Holograms for Projection Images, Optics Express, 2004, p. 2487-2493, vol. 12 No. 11.

Smith et al., Programmable Array Microscopy with a Ferroelectric Liquid-Crystal Spatial Light Modulator, Applied Optics, 2000, p. 2664-2669, vol. 39 No. 16.

Swanson et al., In Vivo Retinal Imaging by Optical Coherence Tomography, Optics Letters, 1993, p. 1864-1866, vol. 18 No. 21.

Xu et al., Confocal Enhanced Optical Coherence Tomography for Nondestructive Evaluation of Paints and Coatings, Optics Letters, 1999, p. 1808-1810, vol. 24 No. 24.

Yamaguchi et al., Phase-Shifting Color Digital Holography, Optics Letters, 2002, p. 1108-1110, vol. 27 No. 13.

* cited by examiner

METHOD OF FULL-COLOR OPTICAL COHERENCE TOMOGRAPHY

CROSS-REFERENCE TO RELATED DISCLOSURES

This disclosure claims priority from a provisional application filed Feb. 20, 2004, entitled: "Method and Apparatus for Full-Color Two-Dimensional Optical Coherence Tomography," bearing application No. 60/546,408. Priority is also claimed to a second provisional application filed Dec. 10, 2004 entitled: "Full-Color Three-Dimensional Microscopy by Wide-Field Optical Coherence Tomography" bearing application No. 60/635,162.

BACKGROUND OF INVENTION

In the field of biomedical imaging, various methods of optical imaging of biomedical tissues known in the art offer significant advantages over other biomedical imaging approaches. These advantages include non-ionizing radiation, wide range of resolution, numerous and effective contrast mechanisms, and relatively compact and inexpensive instrumentation. Optical imaging can be applied to a wide range of biological systems, from cells and subcellular organelles, in vivo and ex vivo tissues, to organs and whole body of a subject, covering the length scales of nanometers and micrometers to millimeters and centimeters. The contrast mechanisms include absorption, transmission, polarization, fluorescence, phase interference, nonlinear and multiphoton processes, as well as time behavior of these processes. Another very important dimension in optical imaging is the effect of these processes as functions of the wavelength of the light—i.e. the spectroscopy of the images. Through spectral imaging, one can monitor for detailed biochemical and biomedical parameters of the specimen.

Optical microscopy and its applications in biomedical imaging have been experiencing a remarkable growth over past few decades, thanks to such technological developments as lasers and digital acquisition and processing of images. One of the main thrust areas of the development of modem microscopy is three-dimensional microscopy, where one acquires a three-dimensional image with every image plane sharply in focus. This is in contrast to conventional microscopy where the image of the in-focus plane is superposed with a blurred image of out-of-focus planes.

In confocal scanning microscopy, CSM, the out-of-focus signal is spatially filtered out by confocal aperturing of the object illumination and the detector points. The three-dimensional image is constructed by pixel-by-pixel mechanical scanning of the entire object volume, which places a fundamental limit on the image acquisition speed.

Another more recent development in 3D microscopy is optical coherence tomography (OCT), where the axial resolution of a few μm is provided by interferometric measurement of the time-of-flight of short-coherence light. In a typical arrangement, a Michelson-type interferometer is illuminated by femtosecond laser or superluminescent LED, and the reference arm is dithered to generate a heterodyne signal in the interference with the back-scattered light from the sample point. The two- or three-dimensional image is constructed from the mechanical scanning over the sample area or volume, as in confocal scanning microscopy. In order to maintain the high speed of the z-scan, a considerably large depth of field, approximately a mm, is needed, which compromises the lateral resolution to a few μm. It is known in the art to sue a confocal adaptation to improve the resolution. The heterodyne detection allows for very high sensitivity and unique capabilities such as Doppler velocity detection of blood flow. OCT-based imaging systems are being developed for diverse areas of medical imaging including retinal structures, endoscopy of gastrointestinal tract and catheter-based intravascular imaging. As a coherent imaging technique, the OCT is capable of penetrating a larger distance into highly scattering media such as biological tissues and ceramics.

Scanning microscopies, including the confocal microscopy and optical coherence tomography, have a number of distinct advantages such as relaxed requirements on the imaging optics and high sensitivity and high resolution. On the other hand, the mechanical scanning is a major limiting factor in the image acquisition speed. Parallel acquisition of two-dimensional images while maintaining the optical sectioning characteristics of CSM or OCT would have obvious advantages. In CSM, such 2D imaging is approximated with a large number of well-spaced apertures, such as rotating Nipkow disk or multi-aperture scanning using an electro-optic spatial light modulator, but the light efficiency or image contrast tends to be low. Wide field optical sectioning is also achieved by structured light microscopy where a moving grating pattern illuminates the object and processing of several images extracts the in-focus sectioned image.

With OCT, it is known that full-field interferometric images can be acquired using broadband light sources, and the regions of the image that do contain interferometric information can be extracted by digital processing of the CCD images, thus generating optical section images variously known as wide-field, full-field, or two-dimensional OCT. The 3D image is constructed by mechanical scanning of the axial direction only. In a simple 2DOCT system, the light source illuminates the entire area of object to be imaged and its interference with the reference beam is imaged using a CCD array. For example, the reference optical path length is modulated by half wavelength, and pair of images is taken with a □ phase shift between them. The difference image then highlights the areas of interference within an axial depth equal to the coherence length, while the rest of the image area is significantly attenuated. A quasi-lock-in image acquisition is known in the art demonstrating synchronous illumination, instead of synchronous detection, due to the limited frame rate of the CCD camera, 30 Hz. High-frequency (50 kHz) true lock-in image acquisition has also been demonstrated in the art using custom made smart array detector, although with a limited number of pixels (58×58).

As such, the prior art demonstrates the potential for high-speed high-resolution 3D microscopy with very respectable sensitivity or dynamic range, at least ~80 db, and promises to have significant impact on OCT applications where acquisition speed is critical, as in real-time in-vivo ophthalmic and endoscopic imaging.

Unlike conventional microscopy, most of the current developments of 3D microscopy usually discard the natural color information of the object, whereas in some of the critical application areas of OCT such as ophthalmic and dermatological imaging, the color and texture of relatively thin top layers of the tissues can provide vital information in a format that is familiar to medical specialists in these areas.

Accordingly, what is needed in the art is a full-color 3D microscopic imaging system and method utilizing wide-field optical coherence tomography resulting in a 3D image with full natural color representation.

However, in view of the prior art considered as a whole at the time the present invention was made, it was not obvious to those of ordinary skill in the pertinent art how the identified need could be fulfilled.

SUMMARY OF INVENTION

In accordance with the present invention a novel method of optical tomography for surface and sub-surface imaging of biomedical tissues is provided. The method is based on the principle of wide field optical coherence tomography (OCT) and is capable of providing full-color three-dimensional views of a tissue structure with high-resolution and high frame rate.

In a particular embodiment, the three-dimensional profile and structure of microscopic objects are obtained by processing CCD images of an object in an interferometric apparatus.

In an additional embodiment, a novel method of full color two-dimensional optical coherence tomography is provided for surface and sub-surface imaging of biomedical tissues. The method as described is based on the principle of wide field optical coherence tomography and is capable of providing full-color two-dimensional and three-dimensional images of a tissue structure with high-resolution and high frame rate.

In an exemplary embodiment, contour or tomographic images are obtained with a phase locked interferometric imaging system using broadband light sources and tri-color cameras. The interferometric images are analyzed in the three-color channels and recombined to generate 3D microscopic images of tissue structures with full natural color representation. In contrast to most existing biomedical optical tomographic methods, the proposed technique allows monitoring of tissue structures close to its natural color, and can provide critical information on the physiological and pathological states of tissues, such as in the retinal tissues affected by glaucoma.

In another exemplary embodiment in accordance with the present invention, full-color 3D microscopic imaging by WFOCT (wide-field optical coherence tomography) is provided using three color LED's. The WFOCT imaging is performed on an object three times using red, green, and blue LED's, and the resulting three RGB channels of the 3D images are combined to generate a final 3D image with full natural color representation.

BRIEF DESCRIPTION OF THE DRAWINGS

The patent application file contains at least one drawing executed in color. Copies of the patent or patent application publication with color drawings will be provided by the Office upon request and payment of the necessary fee. For a fuller understanding of the invention, reference should be made to the following detailed description, taken in connection with the accompanying drawings, in which:

FIG. 3(*a*) is an illustration of the spectra of red, green and blue LEDs and FIG. 3(*b*) is an illustration of the interference profiles of the LEDs vs. the axial distance z;

DETAILED DESCRIPTION OF THE PREFERRED EMBODIMENT

In the following detailed description of the preferred embodiments, reference is made to the accompanying drawings, which form a part hereof, and within which are shown by way of illustration specific embodiments by which the invention may be practiced. It is to be understood that other embodiments may be utilized and structural changes may be made without departing from the scope of the invention.

Figure 1:
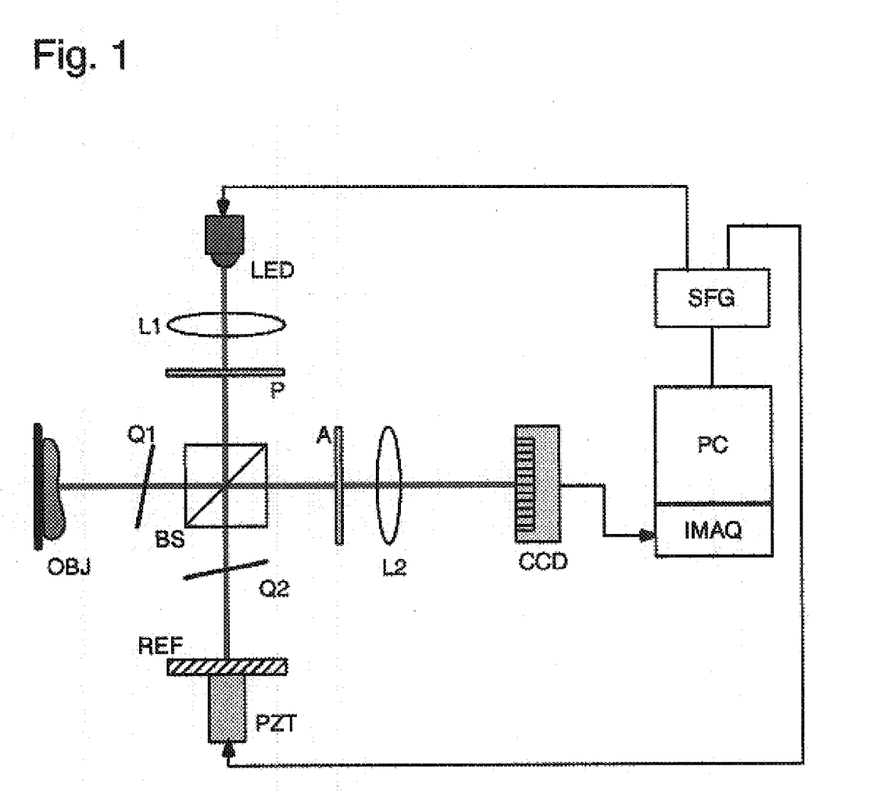
FIG. 1 is an exemplary for color wide-field optical coherence tomography in accordance with the present invention.

The principle of color 3D microscopy by wide-field optical coherence tomography (WFOCT) is described referring to the diagram of the apparatus illustrated in FIG. 1. A high-brightness LED (~30 lumens) illuminates the Michelson interferometer through a collimating lens L1, a polarizer P, and the broadband polarizing beam splitter BS. The quarterwave plates Q1 and Q2 in the object or reference arms change the orthogonal polarization states, so that all of the reflections from the object or the reference mirror are steered toward the monochrome CCD camera through the imaging lens L2. The analyzer A combines the two beams into a common polarization to affect the interference between them. The combination of the polarizer and the analyzer allows continuous adjustment of the relative intensity and the interference contrast between the object and reference beams. The computer acquires the CCD image using an image acquisition board and a function generator is used to strobe the LED and to dither the reference mirror mounted on a piezo-transducer. The object is mounted on a three-axis micrometer translation stage to bring the appropriate object plane into focus.

The reference mirror is positioned at an equal distance with respect to the object focal plane within the coherence length of the LED, and the object contour is imaged by phase-shift interferometry. The light intensity distribution I(x,y) on the CCD array is written as:

$$I = I_O(x, y) + I_B(x, y) + I_R(x, y) + 2\sqrt{I_O(x, y)I_R(x, y)} \cos[\varphi_i + \varphi(x, y)] \quad (1)$$

where $I_O(x, y)$ is the portion of the object reflection that is coherent with respect to the reference $I_R(x,y)$ and $I_B(x, y)$ is the incoherent background. $\Phi(x, y)$ is the relative phase profile between the object and the reference beams, whereas $\Phi_i$ is the phase shift introduced by the piezo-driven reference. The reference mirror is dithered by a sawtooth wave applied to the reference piezo mount over a few micron amplitude. Four image frames are acquired at quarter wavelength intervals corresponding to reference phases of $\Phi_i=0$, $\lambda/2$, $\lambda$, and $3\lambda/2$. These interference images are expressed as:

$$I_0 = I_O + I_B + I_R + 2\sqrt{I_O I_R} \cos\varphi \quad (2)$$

$$I_{\pi/2} = I_O + I_B + I_R - 2\sqrt{I_O I_R} \sin\varphi$$

$$I_\pi = I_O + I_B + I_R - 2\sqrt{I_O I_R} \cos\varphi$$

$$I_{3\pi/2} = I_O + I_B + I_R + 2\sqrt{I_O I_R} \sin\varphi$$

The amplitude of the coherent object image is then given by $$I_O = \frac{(I_0 - I_\pi)^2 + (I_{\pi/2} - I_{3\pi/2})^2}{16 I_R} \quad (3)$$

and the phase map $$\varphi = \tan^{-1} \frac{I_{3\pi/2} - I_{\pi/2}}{I_0 - I_\pi} \quad (4)$$

Figure 2:
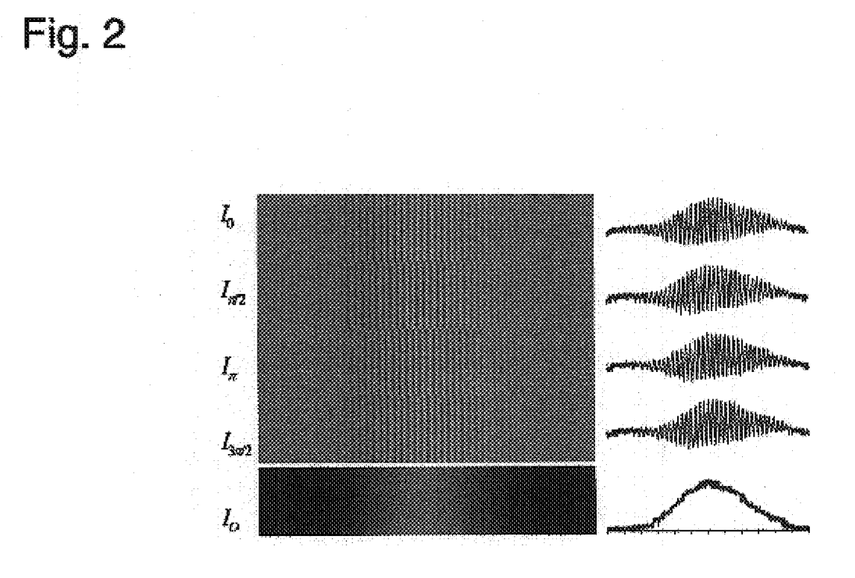
FIG. 2 is an illustration of phase-shift interference imaging in which four quadrature phase interferograms and the extracted interferences images are shown, as well as cross-sectional profiles of the interferograms.
Figure 3:
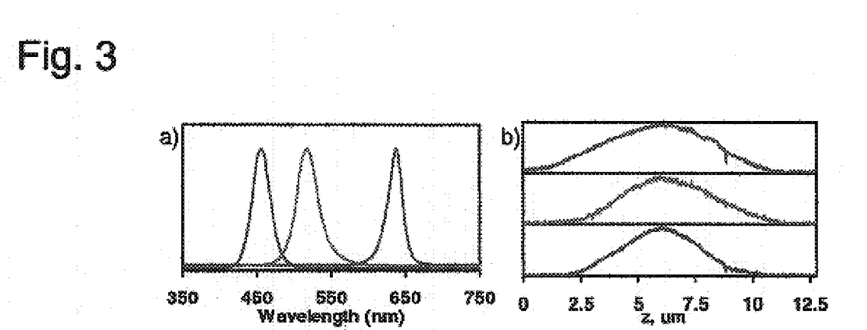

In FIG. 2, a plane mirror is used as the object, tilted by a small angle with respect to the optical axis. The four interference images show that the fringes are shifted by quarter periods. The interference profiles are also plotted in FIG. 2. The bottom image and curve show the envelope of the interference profile as obtained by Eq. (3). The coherence length of the light source can be determined by comparing the width of the interference profile with the fringe periods. They are found to be $\delta_R=5.8$ μm, $\delta_G=4.8$ μm, and $\delta_B=4.0$ μm for the three red, green, and blue LED's, respectively. The normalized spectra and the interference profiles of the LED's are shown in FIG. 3. The center wavelengths of the LED's are $\lambda_R=638.4$ nm, $\lambda_G=528.5$ nm, and $\lambda_B=457.4$ nm, while the spectral widths are $\lambda_R=22.9$ nm, $\Delta_G=33.2$ nm, and $\Delta_B=28.6$ nm. The measured coherence lengths are consistent with the expected values of $(2 \ln 2/\pi)\lambda^2/\Delta$ within a factor of 1.3.

Figure 4:
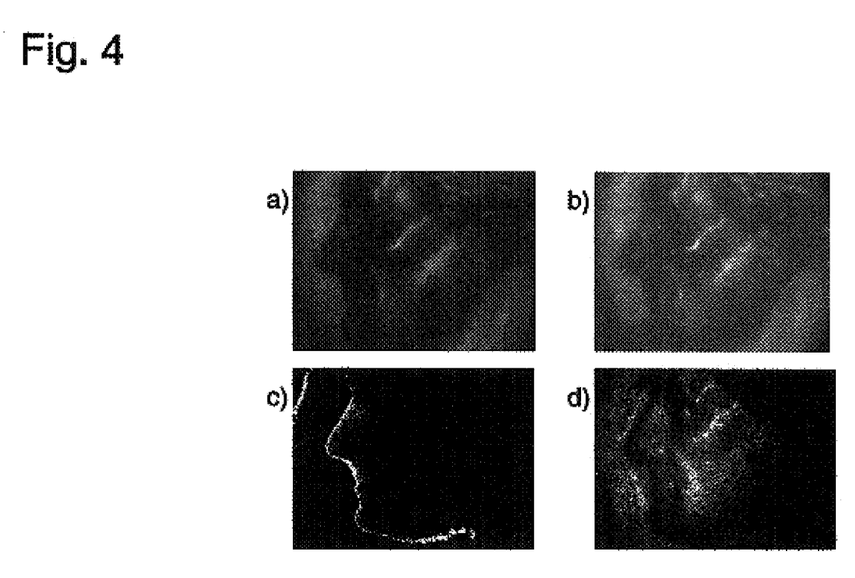
FIG. 4 is an illustration of the phase-shift interference imaging of a coin surface in accordance with the present invention in which, a) is a direct image of the object; b) is an image of the object with the reference wave; c) is an illustration of the contour image extracted by the phase-shift interference; d) is a flat view of the accumulated contour images and where the image volume=12 mm×9 mm×405 µm; voxels=640×480×82; voxel volume=19 µm×19 µm×5 µm.

FIG. 4 illustrates the WFOCT by phase-shifting interferometry using a coin surface as the test object. FIG. 4a) is the direct image of the object in the absence of the reference wave, while FIG. 4b) is when the reference wave is present. Although the two images are mostly indistinguishable, one can observe fluctuating speckles in portions of the object when the camera image is viewed in real time while the reference mirror is dithered. The coherent portion of the image is extracted as described above to obtain a contour of the object at a height that corresponds to the reference mirror position, as shown in FIG. 4c). The contour imaging is repeated a number of times (~40) and averaged to improve the signal-to-noise ratio. The three dimensional imaging is completed by stepping the object z-position over a desired range to obtain a stack of the contour images. The three-dimensional image can then be presented in a number of different ways. In FIG. 4d) all the contour images are added together resulting in a 'flat view', where all the image planes are in focus and additionally the overall haze in FIG. 4a) or b) due to stray reflections from various optical surfaces has been removed.

In an exemplary embodiment, for generation of color images in accordance with the present invention, the WFOCT procedure is repeated three times by using red, green, and blue LED's. Each of these generates a three-dimensional image of the object under the respective color illumination. The three 3D images are then combined as RGB channels to generate the final 3D image with full natural color representation of the volume.

Figure 5:
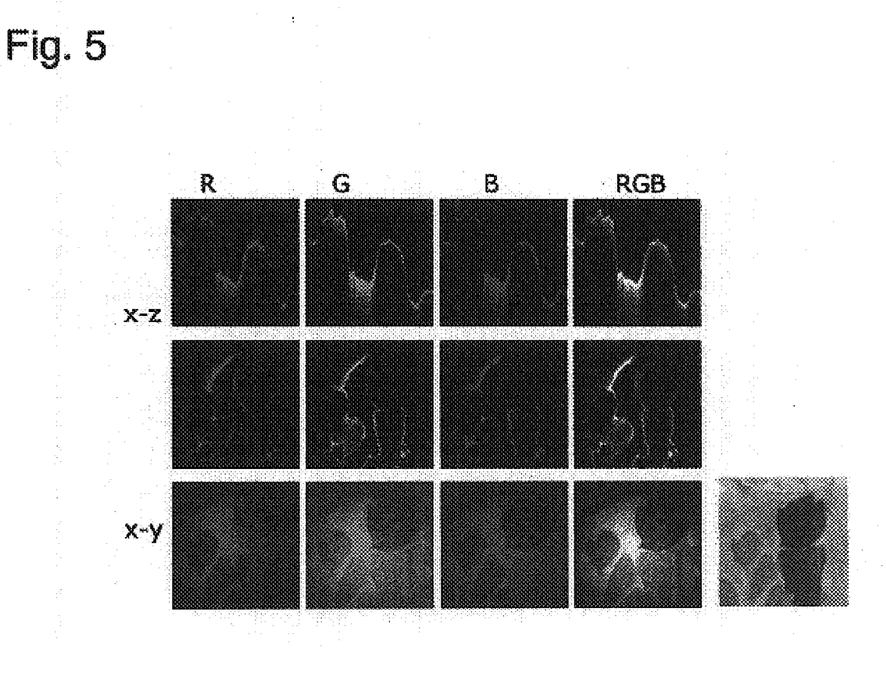
FIG. 5 is an illustration of the color WFOCT of a painted coin surface in accordance with the present invention.
Figure 6:
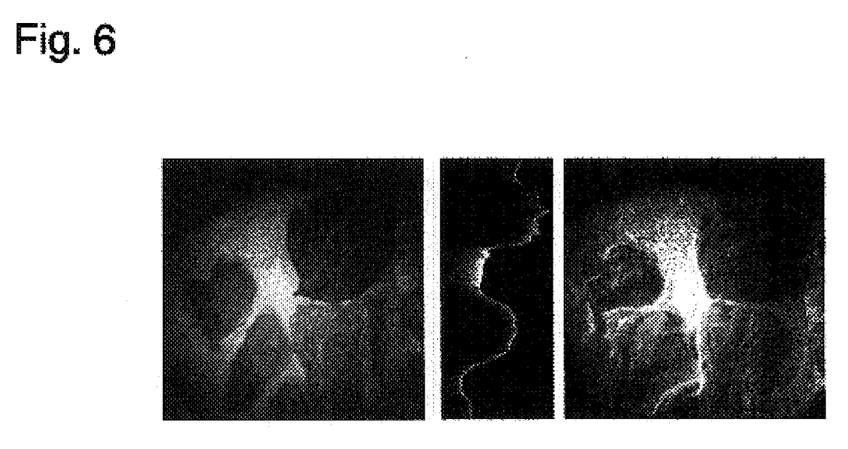
FIG. 6 is an illustration of the color WFOCT movies of a painted coin surface in which a) (1.17 MB) xy-section images; b) (0.26 MB) xz-section images; c) (0.90 MB) 3D perspective views and where the image volume=7.2 mm×7.2 mm×335 µm; voxels=480×480×67; voxel volume=15 µm×15 µm×5 µm.

FIG. 5 and FIG. 6 illustrate experimental results in accordance with an embodiment of the present invention in which a colored coin is used as the test object. The backside of a dime is painted with red, green, and blue ink and the background is painted white. The first three columns of FIG. 5 represent separate results obtained using the three different LED's. In each column, the top square is a 7.2 mm×335 μm xz-section view of the 3D image, the middle square is a 7.2 mm×7.2 mm xy-section or a contour image, while the bottom square is the flat view for the color channel. The last column is the RGB composite images. In FIG. 6, the 3D image is presented in a few different modes. FIG. 6a) is a series of xy-sections and FIG. 6b) is a series of xz-sections. In FIG. 6c) the reconstructed 3D image is viewed from varying perspective angles. Notice the strong color-independent (white) reflection at the air-paint interface and strong colored reflection from underneath. Penetration depth in some areas is at least about 100 μm. In the x-z RGB image, top right corner of FIG. 5, the thin and abrupt layer of red probably accounts for thin layer of paint on the metal surface, whereas there is a pool of white paint in the valley next to it. Also note that the RGB flat image has very respectable color and image quality, compared to the direct photographic image in the lower right corner of FIG. 5.

Figure 7:
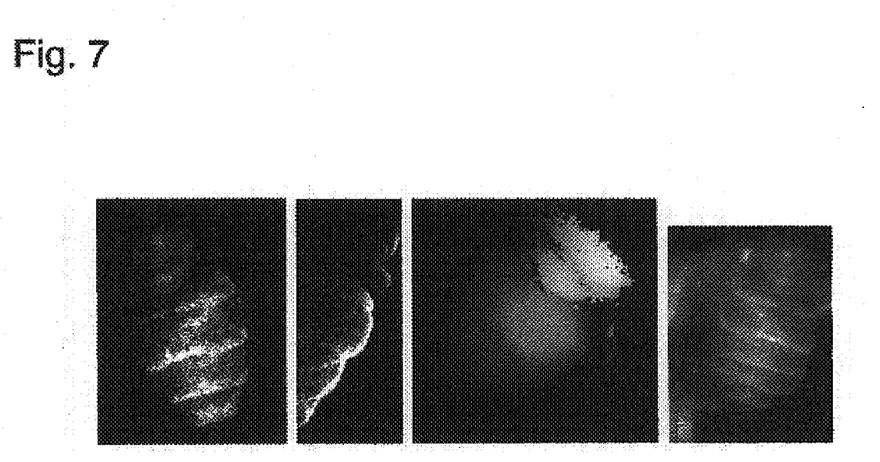
FIG. 7 is an illustration of a monochrome WFOCT movies of a bee in which a) (0.73 MB) xy-section images; b) (0.26 MB) xz-section images; c) (0.64 MB) 3D perspective views; d) direct image of the specimen and where the image volume=6.0 mm×7.8 mm×980 µm; voxels=400×520×99; voxel volume=15 µm×15 µm×10 µm.
Figure 8:
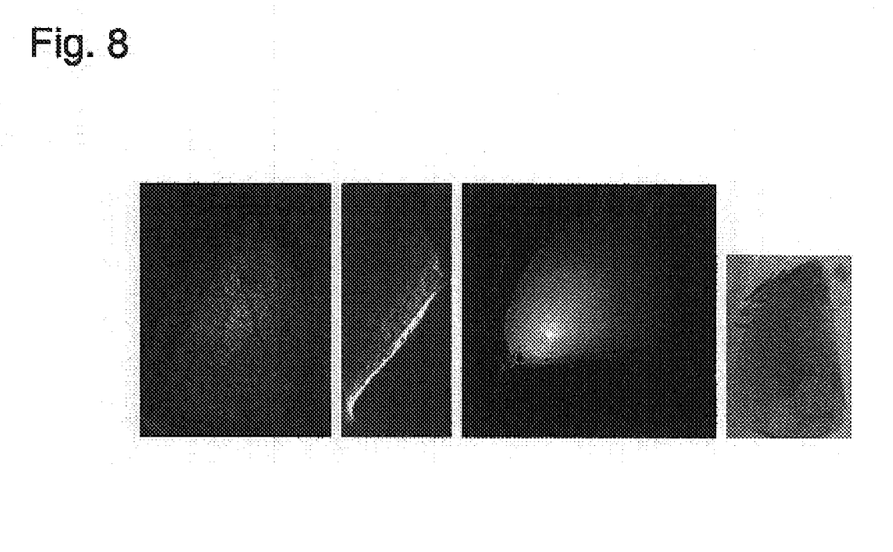
FIG. 8 is an illustration of color WFOCT movies of an insect wing in which a) (0.81 MB) xy-section images; b) (0.38 MB) xz-section images; c) (0.78 MB) 3D perspective views; d) direct image of the specimen and where the image volume=7.2 mm×9.7 mm×810 µm; voxels=480×640×82; voxel volume=15µm×15 µm×10 µm.

Two examples of biological imaging by monochrome WFOCT are shown with reference to FIG. 7 and FIG. 8. FIG. 7 is an image of the body of a bee and FIG. 8 is an image of the wing of an unidentified insect. The XY- and XZ-section movies start with the flat view followed by a series of cross-sectional tomographic views in the respective directions. The image volumes are several millimeters in the lateral direction and less than a millimeter in the longitudinal direction. The relatively opaque body of the bee is seen to have a penetration depth of about 100 μm or so, whereas it is a few hundred microns for the more transparent wing. The typical signal to noise ratio of these images has been measured to be between approximately 50 and 60 db.

Figure 9:
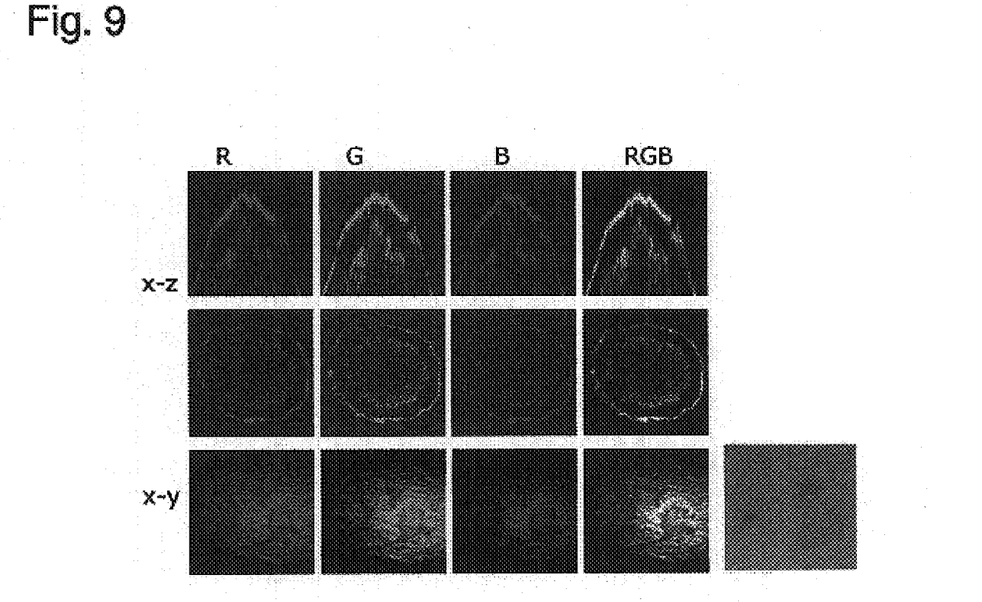
FIG. 9 is an illustration of a color WFOCT of a piece of apple skin in accordance with the present invention.
Figure 10:
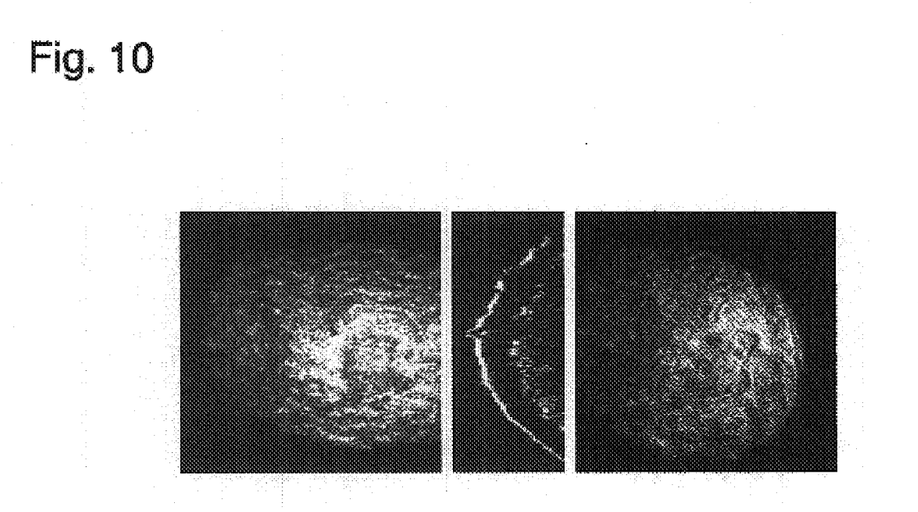
FIG. 10 is an illustration of a color WFOCT movies of apple skin in which a) (0.27 MB) xy-section images; b) (0.10 MB) xz-section images; c) (0.90 MB) 3D perspective views and where the image volume=4.7 mm×4.7 mm×170 µm; voxels=313×313×34; voxel volume=15 µm×15 µm×5 µm.

Examples of color 3D microscopy using the three-channel WFOCT in accordance with the present invention are illustrated with reference to FIG. 9. The images shown in FIG. 9 are arranged in the same manner as those identified in FIG. 5, with the XZ- and XY-sectional views and the flat view for each of the three color channels and the RGB composite color images, for a 4.7 mm×4.7 mm×170 µm volume of a piece of apple skin. Here the penetration depth is at least 150 µm, and it displays details of the top surface and the skin tissue. Because of the large difference in the longitudinal and lateral scales, the minute surface texture is seen greatly exaggerated in the flat views. The cross sectional views clearly show the outer skin layer and a portion of the internal tissue layers. One can also notice the correspondence of the internal structure of a blemish area in the x-z sections and flat view images. The extra picture in the lower right corner is a direct photograph of the approximate area of the imaging experiment. Although the color variation of the apple skin is rather subtle and continuous compared to the colored coin experiment, the RGB flat view reproduces the color variation at least approximately. In this data set the colored images are not as one would expect from common macroscopic views of an apple skin. However, under a microscope, the coloring of apple skin appears not as a solid layer of red surface, but the red pigments are embedded as numerous particles in otherwise colorless matrix. Still one observes some variation of color that can be attributed to the actual color variation of the surface. FIG. 10 illustrates the movies for XY- and XZ-sections and the 3D images of the data set.

Figure 11:
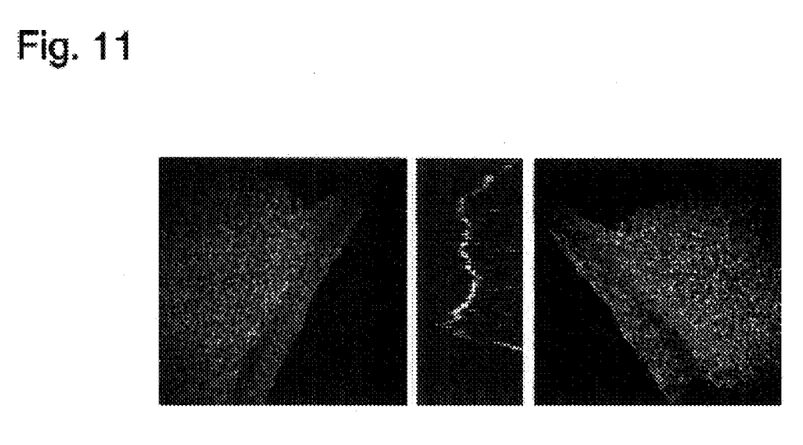
FIG. 11 is an illustration of a color WFOCT movies of a leaf in which a) (0.48 MB) xy-section images; b) (0.15 MB) xz-section images; c) (0.92 MB) 3D perspective views and where the image volume=6.3 mm×6.3 mm×145 µm; voxels=420×420×30; voxel volume=15 µm×15 µm×5 µm.
Figure 12:
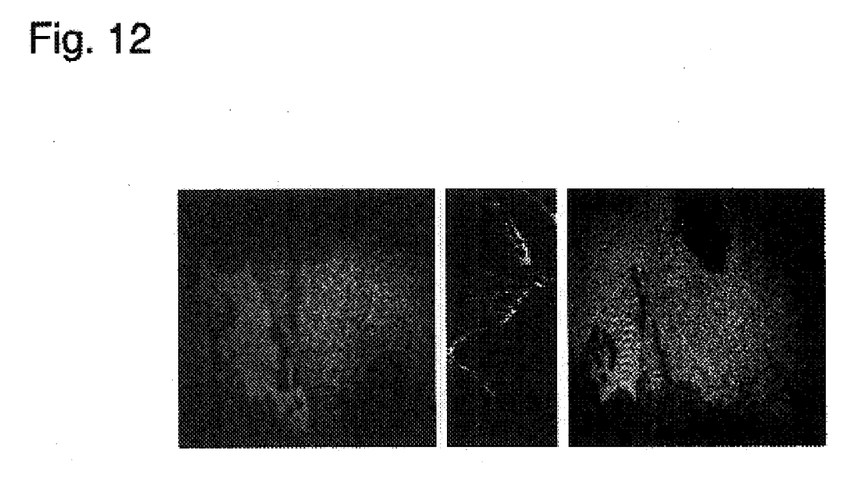
FIG. 12 is an illustrative example of images obtained in accordance with the system and method of the present invention, the images include color WFOCT movies of a leaf, wherein a) (0.065 MB) xy-section images; b) (0.22 MB) xz-section images; c) (0.93 MB) 3D perspective views and wherein image volume=7.2 mm×7.2 mm×190 µm; voxels=480×640×39; voxel volume=15 µm×15 µm×5 µm.

In FIGS. 11 and 12, the color WFOCT in accordance with the present invention is used to generate color 3D images of plant leaves. In FIG. 11, one clearly sees the pattern of pores on the surface as well as a minor stem. A careful examination of the interior of the leaf also shows a fibrous structure running the length of the leaf. In FIG. 12, a piece of scotch tape was present over a part of the leaf in the imaged area. The 3D imaging system clearly imaged through this slightly diffusing layer. As illustrated by these exemplary embodiment and experimental results, the overall quality of the images acquired using the method and apparatus in accordance with the present invention are quite convincing in terms of the resolution, signal level, and the overall capability to generate 3D images with close to natural color information.

The present invention provides a system and method to generate three-dimensional microscopic images with natural color representation. The present invention provides the ability to generate images of biological specimens with about 10 µm axial resolution, about 100–200 µm penetration depth, and 50–60 db dynamic range. These images are generated with close to natural color representation.

Optical section (or tomographic) imaging and imaging through turbid media are very active areas of current research. The method of full color WFOCT microscopy in accordance with the present invention can be used for the generation of optical section images in a wide range of fields of study including biology, medicine, geology, material sciences, and microelectronics. Optical sectioning or tomographic capabilities allow generation of images with the entire 3D volume of the object sharply in focus. The color imaging techniques provided by the method of the present invention provide additional critical information in many of these application areas. Some of the foreseeable applications in biomedicine will be in the imaging of the eyes, the optical biopsy of external tissues, and epithelial layers of gastrointestinal and pulmonary tissues.

It will be seen that the advantages set forth above, and those made apparent from the foregoing description, are efficiently attained and since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween. Now that the invention has been described.

What is claimed is:

1. A method of generating an object image by optical coherence tomography with natural color representation, the method comprising the steps of:
    performing optical coherence tomography imaging on the object illuminated with a red LED resulting in a first image;
    performing optical coherence tomography imaging on the object illuminated with a blue LED resulting in a second image;
    performing optical coherence tomography imaging on the object illuminated with a green LED resulting in a third image; and
    combining the first, second and third images to generate a fourth image having full natural color representation.

2. The method of claim 1, wherein the step of performing optical coherence tomography imaging on the object illuminated with a red LED further comprises the steps of:
    illuminating the object with a reference wave;
    performing phase-shift interference imaging resulting in four image frames acquired at quarter wavelength intervals of the reference wave;
    extracting the first image from the resulting four image frames.

3. The method of claim 1, wherein the step of performing optical coherence tomography imaging on the object illuminated with a red LED further comprises the steps of:
    illuminating the object with a reference wave;
    positioning the object at a first z-position;
    performing phase-shift interference imaging resulting in four first z-position image frames acquired at quarter wavelength intervals of the reference wave;
    extracting a first z-position image from the resulting four first z-position image frames;
    positioning the object at a plurality of z-positions over a predetermined range resulting in a plurality of four z-position image frames acquired at quarter wavelength intervals of the reference wave; and
    extracting the first image from the resulting plurality of z-position four image frames resulting in a three-dimensional image of the object.

4. The method of claim 1, wherein the step of performing optical coherence tomography imaging on the object illuminated with a blue LED further comprises the steps of:
    illuminating the object with a reference wave;
    performing phase-shift interference imaging resulting in four image frames acquired at quarter wavelength intervals of the reference wave;
    extracting the first image from the resulting four image frames.

5. The method of claim 1, wherein the step of performing optical coherence tomography imaging on the object illuminated with a blue LED further comprises the steps of:
   illuminating the object with a reference wave;
   positioning the object at a first z-position;
   performing phase-shift interference imaging resulting in four first z-position image frames acquired at quarter wavelength intervals of the reference wave;
   extracting a first z-position image from the resulting four first z-position image frames;
   positioning the object at a plurality of z-positions over a predetermined range resulting in a plurality of four z-position image frames acquired at quarter wavelength intervals of the reference wave; and
   extracting the first image from the resulting plurality of z-position four image frames resulting in a three-dimensional image of the object.

6. The method of claim 1, wherein the step of performing optical coherence tomography imaging on the object illuminated with a green LED further comprises the steps of:
   illuminating the object with a reference wave;
   performing phase-shift interference imaging resulting in four image frames acquired at quarter wavelength intervals of the reference wave;
   extracting the first image from the resulting four image frames.

7. The method of claim 1, wherein the step of performing optical coherence tomography imaging on the object illuminated with a green LED further comprises the steps of:
   illuminating the object with a reference wave;
   positioning the object at a first z-position;
   performing phase-shift interference imaging resulting in four first z-position image frames acquired at quarter wavelength intervals of the reference wave;
   extracting a first z-position image from the resulting four first z-position image frames;
   positioning the object at a plurality of z-positions over a predetermined range resulting in a plurality of four z-position image frames acquired at quarter wavelength intervals of the reference wave; and
   extracting the first image from the resulting plurality of z-position four image frames resulting in a three-dimensional image of the object.

8. The method of claim 1, wherein the first image is a two-dimensional contour image.

9. The method of claim 1, wherein the second image is a two-dimensional contour image.

10. The method of claim 1, wherein the third image is a two-dimensional contour image.

11. The method of claim 1, wherein the fourth image is a two-dimensional contour image.

12. The method of claim 1, wherein the first image is a three-dimensional image.

13. The method of claim 1, wherein the second image is a three-dimensional image.

14. The method of claim 1, wherein the third image is a three-dimensional image.

15. The method of claim 1, wherein the fourth image is a three-dimensional image.

16. The method of claim 1, wherein the object of interest is biological tissue.

17. A method of generating an object image by optical coherence tomography with natural color representation, the method comprising the steps of:
   illuminating an object of interest with a white light source;
   illuminating the object of interest with a reference wave;
   performing phase-shift interference imaging on the object of interest resulting in at least two color image frames acquired at predetermined wavelength intervals of the reference wave;
   separating the color image frames resulting in at least two red image frames, at least two green image frames and at least two blue image frames;
   extracting a red image from the at least two red image frames;
   extracting a blue image from the at least two blue image frames;
   extracting a green image from the at least two green image frames;
   combining the red image, blue image and green image to generate an image having full natural color representation.

18. The method of claim 17, wherein the step of performing phase-shift interference imaging on the object of interest results in four color image frames acquired at quarter wavelength intervals of the reference wave.

19. The method of claim 17, wherein the step of performing optical coherence tomography imaging on the object further comprises the steps of:
   positioning the object at a first z-position;
   performing phase-shift interference imaging resulting in four first z-position color image frames acquired at quarter wavelength intervals of the reference wave;
   extracting a first z-position red image from the resulting four first z-position color image frames;
   extracting a first z-position blue image from the resulting four first z-position color image frames;
   extracting a first z-position green image from the resulting four first z-position color image frames;
   positioning the object at a plurality of z-positions over a predetermined range resulting in a plurality of four z-position color image frames acquired at quarter wavelength intervals of the reference wave;
   extracting the first red image from the resulting plurality of z-position four image frames resulting in a red three-dimensional image of the object;
   extracting the first blue image from the resulting plurality of z-position four image frames resulting in a blue three-dimensional image of the object.
   extracting the first green image from the resulting plurality of z-position four image frames resulting in a green three-dimensional image of the object; and
   combining the red three-dimensional image, blue three-dimensional image and green three-dimensional image to generate a three-dimensional image having full natural color representation.

20. The method of claim 17, wherein the object of interest is biological tissue.

* * * * *

UNITED STATES PATENT AND TRADEMARK OFFICE
CERTIFICATE OF CORRECTION

| | | |
|---|---|---|
| PATENT NO. | : 7,095,503 B2 | Page 1 of 1 |
| APPLICATION NO. | : 11/063499 | |
| DATED | : August 22, 2006 | |
| INVENTOR(S) | : Myung K. Kim and Lingfeng Yu | |

It is certified that error appears in the above-identified patent and that said Letters Patent is hereby corrected as shown below:

Please amend the specification as follows:

Please insert the following new paragraph after the Title section: Col. 1, Line 4

STATEMENT OF GOVERNMENT INTEREST

This invention was made with Government support under Grant No. DBI-0243237 awarded by the Natural Science Foundation. The Government has certain rights in the invention.

Signed and Sealed this

Nineteenth Day of December, 2006

JON W. DUDAS
*Director of the United States Patent and Trademark Office*